United States Patent
Black

(10) Patent No.: US 8,777,996 B2
(45) Date of Patent: Jul. 15, 2014

(54) INTERSPINOUS LIGAMENT TRANSVERSE CONNECTOR

(75) Inventor: Michael Black, Swarthmore, PA (US)

(73) Assignee: Globus Medical, Inc., Audubon, PA (US)

( * ) Notice: Subject to any disclaimer, the term of this patent is extended or adjusted under 35 U.S.C. 154(b) by 96 days.

(21) Appl. No.: 13/181,062

(22) Filed: Jul. 12, 2011

(65) Prior Publication Data

US 2012/0010663 A1   Jan. 12, 2012

Related U.S. Application Data

(60) Provisional application No. 61/363,387, filed on Jul. 12, 2010.

(51) Int. Cl.
*A61B 17/88* (2006.01)

(52) U.S. Cl.
USPC .......................................... 606/279; 606/250

(58) Field of Classification Search
USPC ................. 606/248–250, 251–278, 279
See application file for complete search history.

(56) References Cited

U.S. PATENT DOCUMENTS

| | | | |
|---|---|---|---|
| 4,781,190 A * | 11/1988 | Lee | 606/139 |
| 5,010,879 A | 4/1991 | Moriya et al. | |
| 5,354,305 A * | 10/1994 | Lewis et al. | 606/152 |
| 5,380,325 A | 1/1995 | Lahille | |
| 5,569,246 A * | 10/1996 | Ojima et al. | 606/252 |
| 5,676,665 A | 10/1997 | Bryan | |
| 5,865,836 A * | 2/1999 | Miller | 606/228 |
| 6,090,111 A | 7/2000 | Nichols | |
| 6,565,565 B1 | 5/2003 | Yuan et al. | |
| 6,669,729 B2 | 12/2003 | Chin | |
| 6,689,153 B1 * | 2/2004 | Skiba | 606/232 |
| 6,740,086 B2 | 5/2004 | Richelsoph | |
| 6,755,829 B1 | 6/2004 | Bono et al. | |
| 6,786,903 B2 | 9/2004 | Lin | |
| 7,081,117 B2 | 7/2006 | Bono et al. | |
| 7,125,426 B2 | 10/2006 | Moumene et al. | |
| 7,261,714 B2 | 8/2007 | Richelsoph | |
| 7,282,064 B2 | 10/2007 | Chin | |
| 7,699,873 B2 * | 4/2010 | Stevenson et al. | 606/250 |
| 7,875,063 B1 * | 1/2011 | Sander et al. | 606/300 |
| 8,034,082 B2 * | 10/2011 | Lee et al. | 606/250 |
| 8,202,299 B2 * | 6/2012 | Wang et al. | 606/246 |
| 2002/0120272 A1 | 8/2002 | Yuan et al. | |
| 2005/0080416 A1 | 4/2005 | Ryan et al. | |
| 2005/0119657 A1 | 6/2005 | Goldsmith | |
| 2005/0228326 A1 | 10/2005 | Kalfas et al. | |
| 2006/0009766 A1 * | 1/2006 | Lee et al. | 606/61 |
| 2006/0200128 A1 | 9/2006 | Mueller | |
| 2007/0233089 A1 * | 10/2007 | DiPoto et al. | 606/61 |
| 2007/0299446 A1 | 12/2007 | Chin | |
| 2008/0045955 A1 | 2/2008 | Berrevoets et al. | |
| 2010/0204732 A1 * | 8/2010 | Aschmann et al. | 606/249 |

* cited by examiner

*Primary Examiner* — Jan Christopher Merene

(57) ABSTRACT

The present invention includes the steps for creating an access path to the posterior portion of the spine, positioning a first and second elongate rod longitudinally on opposing portions of the spine, piercing a portion of the interspinous ligament with a third elongate rod, and positioning the third elongate rod connecting the first and second elongated rods in a cross connection assembly. The cross connection assembly includes a one-piece connecting body comprising a receptacle facing outwards towards the first rod and away from the second rod and a clamp, and a set screw selectively positioned to securely hold the connecting body to the first rod. The connecting body is disposed substantially between the first and second elongate rods. The clamp allows the connecting body to slidingly engage with the third rod.

7 Claims, 6 Drawing Sheets

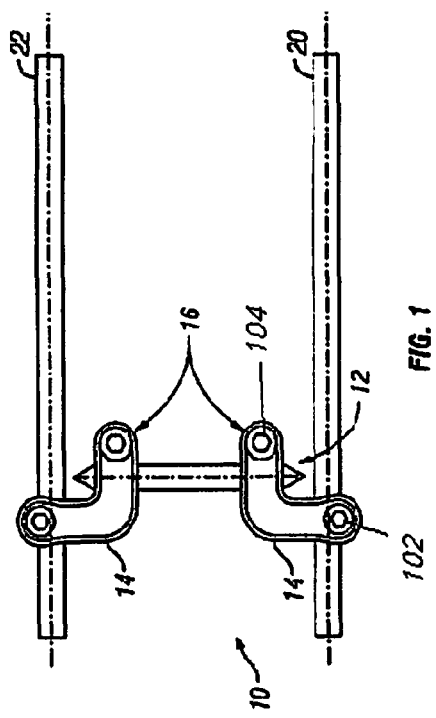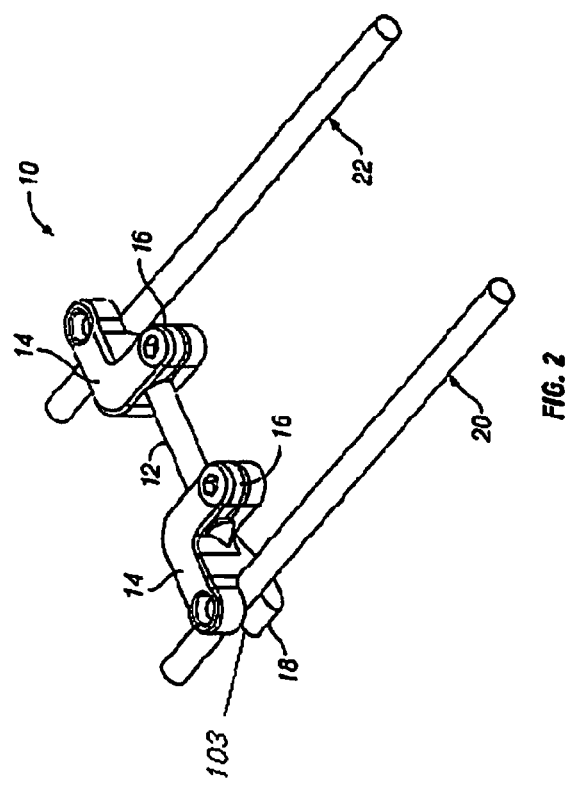

INTERSPINOUS LIGAMENT TRANSVERSE CONNECTOR

CROSS-REFERENCE TO RELATED TO APPLICATIONS

This application is a non-provisional application claiming priority to provisional application Ser. No. 61/363,387 filed on Jul. 12, 2010, incorporated herein in its entirety.

FIELD OF THE INVENTION

The present invention relates to device which stabilizes the spine. In particular, the present invention is related to stabilizing the spine through the use of rods and rod connectors.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. Often, these irregularities are treated by immobilizing a portion of the spine. This treatment typically involves affixing a plurality of screws and/or hooks to one or more vertebrae and connecting the screws or hooks to an elongate rod that generally extends in the direction of the axis of the spine.

Treatment for these spinal irregularities often involves using a system of pedicle screws and rods to attain stability between spinal segments. Instability in the spine can create stress and strain on neurological elements, such as the spinal cord and nerve roots. In order to correct this, implants of certain stiffness can be implanted to restore the correct alignment and portion of the vertebral bodies. Surgeons utilize polyaxial bone screws throughout the spine for posterior fusion. The rigidity or stiffness of posterior fusion systems is commonly augmented by the use of trans-connectors or t-connectors. The screw trajectory and placement is often dictated by the natural anatomy and frequently results in situations where the polyaxial bone screws are very close or even touch the adjacent screws.

In the abovementioned situation, a standard t-connector or trans-connector that affixes directly onto the titanium alloy rods may not be suitable due to the proximity of the bone screws. There is a need for a transverse connector which would be ideally suited to provide rigidity to the construct by puncturing through the interspinous ligament.

SUMMARY OF THE INVENTION

The present invention provides a method for stabilizing the spine including the steps for creating an access path to the posterior portion of the spine, positioning a first and second elongate rod longitudinally on opposing portions of the spine, piercing a portion of the interspinous ligament with a third elongate rod, and positioning the third elongate rod connecting the first and second elongated rods in a cross connection assembly. The cross connection assembly includes a one-piece connecting body comprising a receptacle facing outwards towards the first rod and away from the second rod and a clamp, and a set screw selectively positioned to securely hold the connecting body to the first rod. The connecting body is disposed substantially between the first and second elongate rods. The clamp allows the connecting body to slidingly engage with the third rod. A fastener 104 causes the clamp to be clamped around the third rod, thereby locking the third rod relative to the connecting body. The third rod is configured and designed with frusto-conical tips for piercing the interspinous ligament.

BRIEF DESCRIPTION OF THE DRAWINGS

The attached drawings illustrate the elements of the present invention. Design and utility features of the present invention are also disclosed.

FIGS. 1-4 illustrate various views of one exemplary embodiment of a transverse connector system according to the present invention;

DETAILED DESCRIPTION OF THE INVENTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to limit the scope of the disclosure, including the claims, is limited to that embodiment.

The interspinous transverse connector is configured and designed to be implanted through the interspinous ligament by a rod that can puncture through the ligament, while at the same time leaving the ligament in tact. Generally, in spinal procedures for implanting trans-connectors systems, the interspinous ligament is removed and a traditional cross connector is positioned. However, there is no need to remove the interspinous ligament, therefore by positioning the present interspinous connector system, stabilizing the spine decreases operating time, and increases the speed of recovery and the bodies natural structures will continue to aid in stabilizing the spine.

Figure 3:
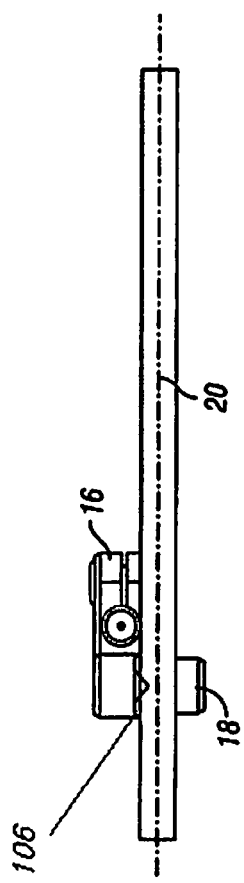
Figure 4:
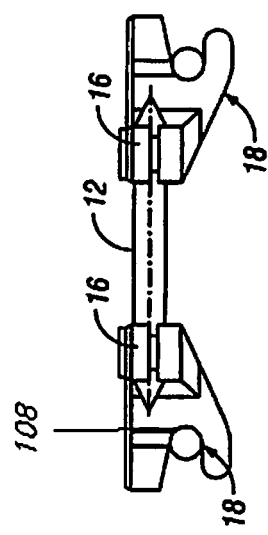

The first embodiment of the present invention, as illustrated in FIGS. 1-4 show a bullet-tipped or frusto-conical ends of a cross connector 10 for puncturing through the interspinous ligament and enables the positioning of the cross connector 10 regardless of the orientation. The rod 12 is fixed to the body 14 of the connector 10 by a clamp 16 provided on opposite sides of the system. Each connector body 14 is provided with a hook 18 on the end for coupling to the posterior rods 20 and 22.

As illustrated in FIGS. 1-4, posterior rods 20 and 22 preferably run along the length of at least two or more vertebrae. Each rod 20 and 22 is preferably fixed to the vertebrae. In order to align the two or more vertebrae, rods 20 and 22 are preferably held in place using, for example, a fixation device. The present invention comprises, as mentioned above, two connecting bodies 14 that are preferably connected using a third rod, which allows the two rods 20 and 22 to be fixed in place relative to one another. Each of the connecting bodies preferably comprise a receptacle 103 having an opening for passing the third rod that is capable of fixing the connecting body in place relative to the third rod using, for example, a screw. The opening preferably includes a c-ring 106 having a spherical curvature, which may be placed within the opening to pass the third rod. The c-ring 106 can comprise a notch 108 selectively positioned on an inner face of the c-ring and substantially opposite the opening. The spherical curvature of the c-ring preferably prevents it from being forced out of the opening under normal conditions. The c-ring is capable of allowing the two connecting bodies to translate axially, or side to side, with respect to the third rod. This allows the spacing between the two rods 20 and 22 to be adjusted during, for example, an operation. Once the two connecting bodies are positioned as desired, they may be fixed in place relative to the third rod.

Figure 5:
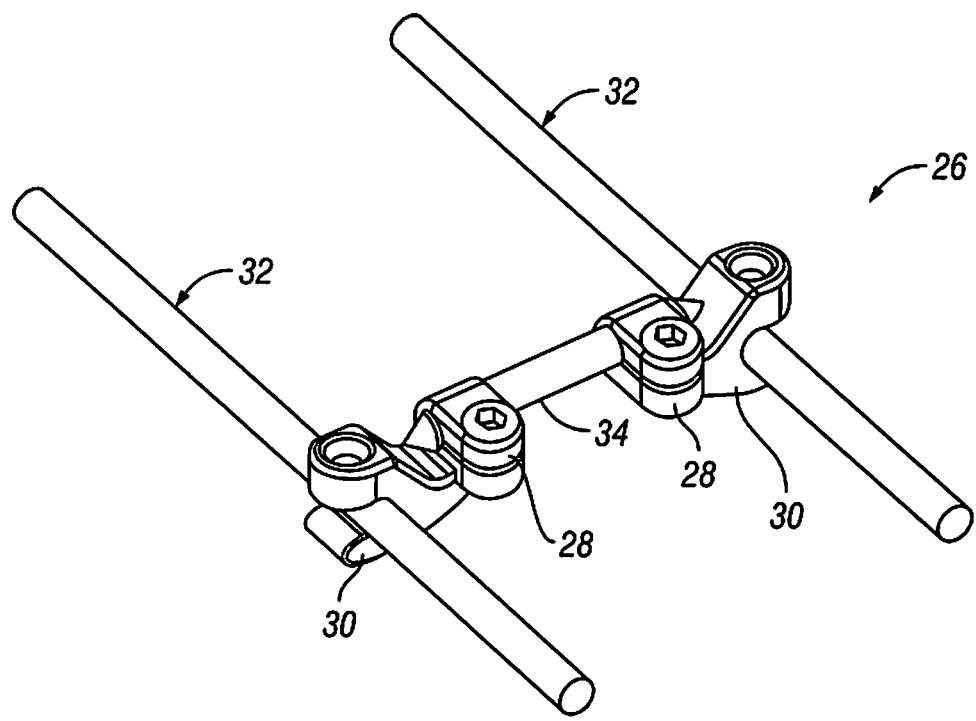
FIGS. 5-8 illustrate yet another embodiment of a transverse connector system according to the present invention.
Figure 6:
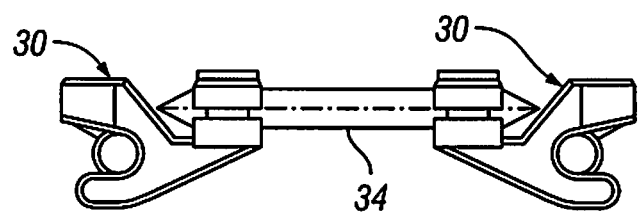
Figure 7:
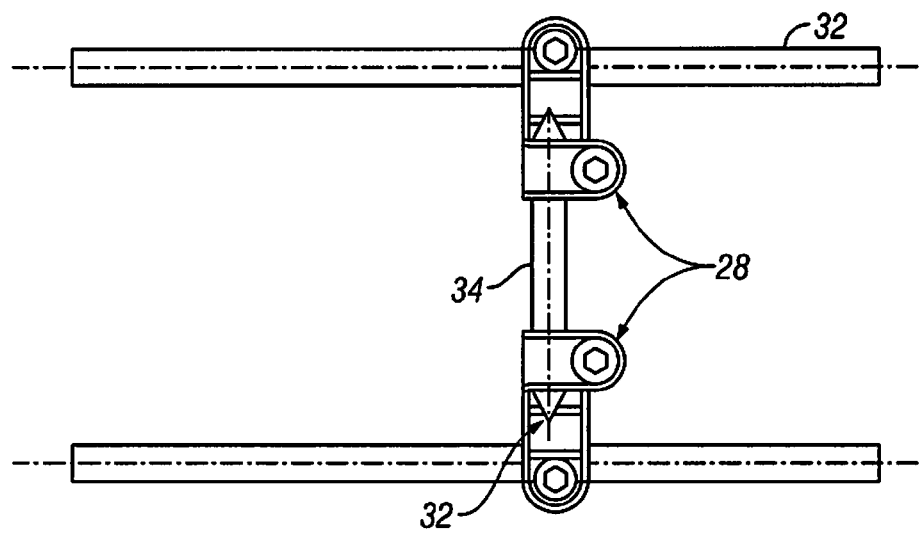
Figure 8:
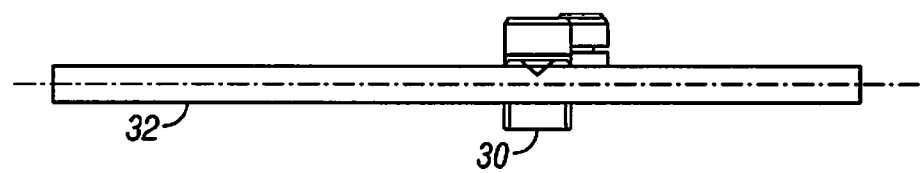

The second embodiment of the present invention, as illustrated in FIGS. 5-8, show a connector system 26 having multiple clamps 28 provided with hooks 30 capable of coupling to posterior rods 32. The cross connector rod 34 is configured to be in-line with the posterior hooks 30 of the clamps 28. The cross connector rod 34 is configured and designed with a frustoconical ends. The cross connector rod 34 is designed so that a surgeon can use the frustoconical ends to pierce the interspinous ligament rather than removing the interspinous ligament.

Figure 9:
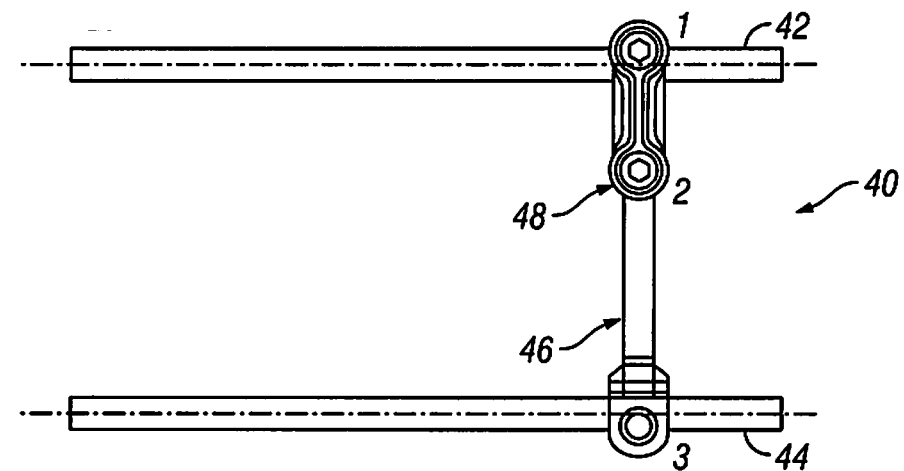
FIGS. 9-12 illustrate yet another embodiment of a transverse connector system according to the present invention.
Figure 10:
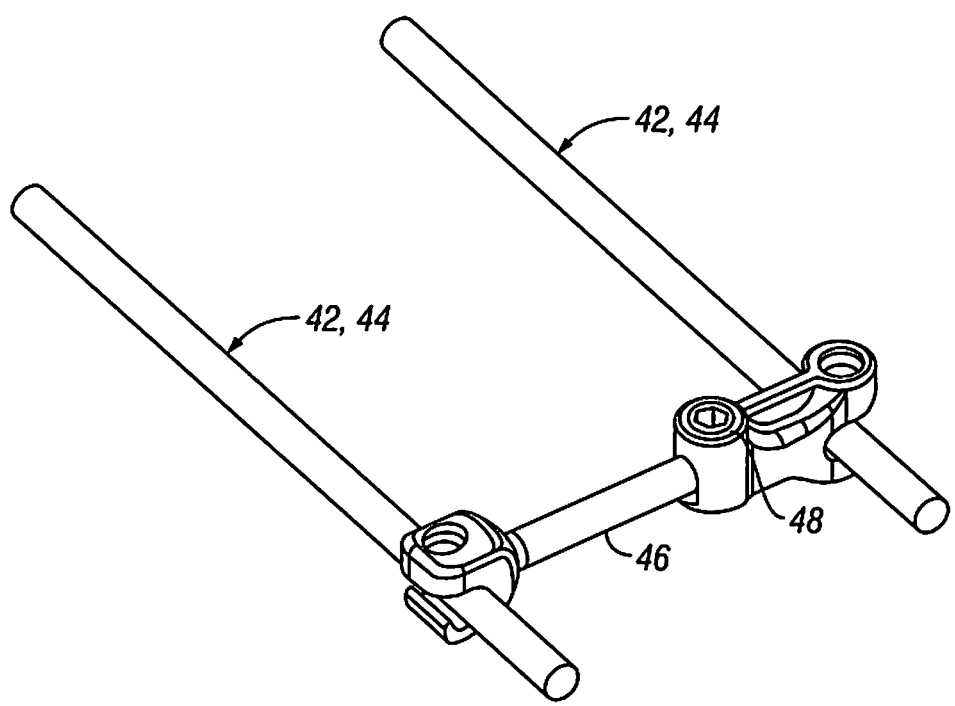
Figure 11:
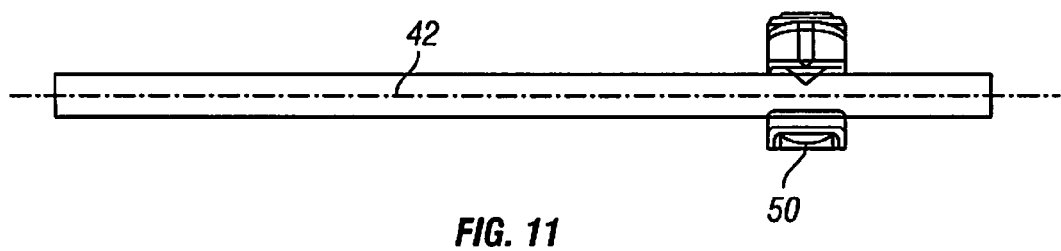
Figure 12:
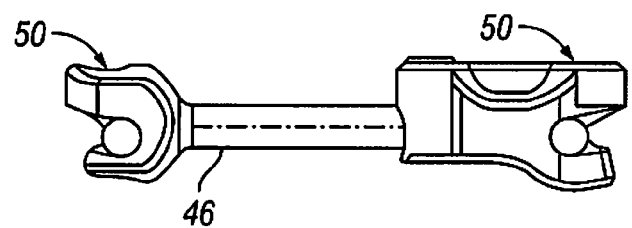

The third embodiment of the present invention, as illustrated in FIGS. 9-12, another inline cross connector system 40 attached to posterior rods 42 and 44. The cross connector 40 in the embodiment is integral to a first portion 46 of the hook end of the connector body of the construct and the locking point 48 for the cross connector is integral to the contra-lateral hook 50 and configured to be inline with the hook itself.

In the embodiments illustrated in FIGS. 1-8, the cross connecting rod is bullet shaped at the ends so that the ends may puncture through the interspinous ligament. In the embodiment illustrated in FIGS. 9-12, a single end of the cross connecting rod is bullet shaped and the other end is integral and/or coupled to the opposite hook portion of the connector assembly. Although the ends of the cross connector rod are bullet shaped, it should be noted that any shape that enables the cross connector rod to puncture through the interspinous ligament may be used. Additionally, it should be noted that the clamps in all the embodiments are tightened using a set screw 102 to secure the rods into their proper position. Also, the hooks at the opposing ends of all the embodiments are also provided with a set screw to tighten down on the posterior rods.

The various features and embodiments of the invention described herein may be used interchangeably with other feature and embodiments. Finally, while it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments which come within the spirit and scope of the present invention.

The invention claimed is:

1. A method for stabilizing the spine, comprising:
   creating an access path to the posterior portion of the spine;
   positioning a first and second elongate rod longitudinally on opposing portions of the spine;
   positioning a cross connector system comprising:
      a third elongate rod, connecting the first and second elongated rods;
      a one-piece connecting body comprising a first elongated portion having first and second ends, a second elongated portion having first and second ends, the second end of the first elongated portion and the first end of the second elongated portion are integrally formed with each other to form an L-shaped body, wherein the first end of the first portion comprises a receptacle facing outwards towards the first rod and away from the second rod and the second end of the second elongated portion comprises a clamp, the clamp comprises an upper clamp portion and a lower clamp portion and an opening therebetween;
   a first set screw selectively positioned to securely hold the connecting body to the first rod;
   a second set screw selectively positioned to securely hold the connecting body to the third rod, wherein the second set screw is located at the second end of the second elongated portion and the first set screw is located at the first end of the first elongated portion such that from a top view of the cross connector system, the second set screw is offset both vertically and horizontally from the first set screw, and
      wherein the connecting body is disposed substantially between the first and second elongate rods;
      wherein the clamp allows the connecting body to slidingly engage with the third rod;
      wherein a fastener causes the clamp to be clamped around the third rod, thereby locking the third rod relative to the connecting body,
      wherein the third rod is configured and designed with frusto-conical tips,
   puncturing an interspinous ligament with the frusto-conical tips of the third rod, wherein the interspinous ligament is punctured in a direction that is transverse to the first and second elongate rods;
   positioning the third rod within the connecting body of the cross connector system; and
   securing the first, second and third rods stabilizing the spine.

2. The method according to claim 1, wherein the connecting body is capable of rotating about a transverse axis.

3. The method according to claim 1, wherein the connecting body is capable of rotating about an axis perpendicular to a transverse axis.

4. A method of stabilizing the spine comprising the steps of:
   positioning a transverse fixation system in a posterior portion of the spine; and
   securing the transverse fixation system to the posterior portion of the spine,
   wherein the transverse fixation system comprises:
      a first and a second elongate rod;
      a first and a second c-ring, each c-ring comprising an outer surface having a spherical curvature and first and second free ends facing each other to define an opening;
      a third elongate rod;
      a first and a second one-piece connecting body, the first and second one-piece connecting bodies each comprising a first elongated portion having first and second ends, a second elongated portion having first and second ends, the second end of the first elongated portion and the first end of the second elongated portion are integrally formed with each other to form an L-shaped, wherein the first end of the first elongated portion comprises a receptacle facing outwards towards either the first rod or second rod and away from the other of the first rod or second rod and the second end of the second elongated portion comprises a clamp,
   wherein the first and second connecting bodies are disposed substantially between the first and second elongate rods;
   a first fastener selectively positioned to securely hold the first connecting body to the first rod;

a second fastener selectively positioned to securely hold the second connecting body to the second rod;
a first set screw capable of securing the first clamp to the third rod;
wherein the first c-ring and first clamp allow the first connecting body to slidingly engage with the third elongate rod;
wherein rotation of the first set screw causes the first clamp to be clamped around the third elongate rod relative to the first connecting body;
a second set screw capable of securing the second clamp to the third rod;
wherein the first fastener is located at the first end of the first elongated portion of the first connecting body, the first set screw is located at the second end of the second elongated portion of the first connecting body, the second fastener is located at the first end of the second elongated portion of the second connecting body, the second set screw is located at the second end of the second elongated portion of the second connecting body such that from a to view of the cross connector system, the first fastener is offset both vertically and horizontally from the first set screw and the second fastener is offset both vertically and horizontally from the second set screw;
wherein the second c-ring and second clamp allow the second connecting body to slidingly engage with the third elongate rod; and
wherein rotation of the second set screw causes the second clamp to be clamped around the third elongate rod relative to the second connecting body;
wherein the first and second c-ring comprise a notch selectively positioned on an inner face of the c-ring and substantially opposite the opening,
wherein the third elongate rod is configured with frusto-conical tips for piercing a portion of the interspinous ligament,
puncturing an interspinous ligament with the frusto-conical tips of the third rod, wherein the interspinous ligament is punctured in a direction that is transverse to the first and second elongate rods.

5. The method according to claim 4, wherein the first and second clamps are capable of holding the first and second connecting bodies in place relative to the third rod.

6. The method according to claim 4, wherein the connecting body is capable of translating axially relative to the third rod.

7. A method for stabilizing the spine, comprising:
creating an access path to the posterior portion of the spine;
positioning a first and second elongate rod longitudinally on opposing portions of the spine;
piercing a portion of the interspinous ligament with a third elongate rod;
positioning the third elongate rod connecting the first and second elongated rods in a cross connection assembly, the cross connection assembly comprising:
a one-piece connecting body comprising a first elongated portion having first and second ends, a second elongated portion having first and second ends, the second end of the first elongated portion and the first end of the second elongated portion are integrally formed with each other to form an L-shaped body, wherein the first end of the first elongated portion comprises a receptacle facing outwards towards the first rod and away from the second rod and the second end of the second elongated portion comprises a clamp, the clamp comprises an upper clamp portion and a lower clamp portion and an opening therebetween;
a set screw selectively positioned to securely hold the connecting body to the first rod; and
wherein the connecting body is disposed substantially between the first and second elongate rods;
wherein the clamp allows the connecting body to slidingly engage with the third rod;
wherein a fastener causes the clamp to be clamped around the third rod, thereby locking the third rod relative to the connecting body, wherein the fastener is located at the second end of the second elongated portion and the set screw is located at the first end of the first elongated portion such that from a top view of the one-piece connecting body, the set screw is offset both vertically and horizontally from the fastener:
wherein the third rod is configured and designed with frusto-conical tips,
wherein the interspinous ligament is pierced in a direction that is transverse to the first and second elongate rods.

* * * * *